United States Patent [19]

Moermann et al.

[11] Patent Number: 4,615,678
[45] Date of Patent: Oct. 7, 1986

[54] BLANK FROM WHICH A DENTAL IMPLANT CAN BE MACHINED, AND A METHOD OF MAKING THE BLANK

[76] Inventors: Werner H. Moermann, Zweiackerstrasse 57, CH-8057 Zuerich; Marco Brandestini, Gartenstrasse 10, CH-8702 Zollikon, both of Switzerland

[21] Appl. No.: 708,309

[22] Filed: Mar. 5, 1985

[30] Foreign Application Priority Data

Mar. 6, 1984 [CH] Switzerland .......................... 1110/84

[51] Int. Cl.$^4$ .............................................. A61C 8/00
[52] U.S. Cl. ................................... 433/201.1; 433/173
[58] Field of Search ......................... 433/180, 201, 173

[56] References Cited

U.S. PATENT DOCUMENTS

| | | | |
|---|---|---|---|
| 4,222,128 | 9/1980 | Tomonaga et al. | 433/201 X |
| 4,223,412 | 9/1980 | Aoyagi et al. | 433/201 X |
| 4,259,072 | 3/1981 | Hirabayashi et al. | 433/201 X |
| 4,411,624 | 10/1983 | Ogino et al. | 433/201 X |
| 4,431,420 | 2/1984 | Adair | 433/201 X |
| 4,457,714 | 7/1984 | Klein | 433/180 |
| 4,511,336 | 4/1985 | Hidaka et al. | 433/173 |

*Primary Examiner*—Nancy A. B. Swisher
*Attorney, Agent, or Firm*—Flynn, Thiel, Boutell & Tanis

[57] ABSTRACT

A blank adapted for use in custom fabrication of an implant for dental restoration includes first and second joined parts. The first part is made of the raw material of the ultimate implant, whereas the second part can be made of a different material. The second part is shaped to facilitate a positive support of the blank in a milling machine, and is preferably equipped with a code-bearing surface which permits information about the physical properties of the blank to be sensed by the machine. In a preferred realization, the first part is made from ceramic silica and the second part from aluminum, and the two are bonded by an acrylic glue.

21 Claims, 4 Drawing Figures

BLANK FROM WHICH A DENTAL IMPLANT CAN BE MACHINED, AND A METHOD OF MAKING THE BLANK

FIELD OF THE INVENTION

The present invention relates to a blank from which a dental implant for use in dental restoration techniques can be made, and a method of making the blank.

BACKGROUND OF THE INVENTION

The present invention relates to the economical production of a blank, preferably made at least partly of a ceramic material, which can be used to fabricate an implant for use in dental restoration. Cavities in teeth are commonly filled or restored by using amalgam, which is the least expensive method, or by using some more elaborate approach such as an inlay, a crown or a more complex structure, which all require access to a laboratory and at least two sessions with the patient.

Copending U.S. patent application Ser. No. 643 755 filed Aug. 23, 1984, the disclosure of which is incorporated herein by reference, discloses a method and apparatus by which, in one session, a ceramic implant can automatically be custom formed and thereafter used to restore the tooth to its original shape and function. The present invention relates to an improved blank from which an implant can be machined by an apparatus of the type disclosed in U.S. Ser. No. 643,755.

Several objectives are to be attained by the present invention. The blank should be well adapted for use in the particular environment, namely a dentist's office. This calls for features which facilitate mass production of the blank, which facilitate ease of handling by the dentist or his/her aide, and which assure the requisite accuracy in the end product.

SUMMARY OF THE INVENTION

These and other objects and purposes of the invention are met by providing a blank which includes a part made of a ceramic material. To make the ceramic part, alumina or, as is more common in the dental setting, silica is pressed to the desired shape and then baked. This produces the desired mechanical strength, but leads to very loose dimensional tolerances, because the parts often shrink and/or deform drastically. It should also be noted that trimming after baking requires special machinery and excessive handling time, typically rendering any trimming procedure uneconomical. In addition, since the blank needs to be supported in the machine, preferably by a quick fastening chuck having for example a friction grip, a second part which is a support stub is attached to the ceramic portion and is adapted to be gripped by the chuck. This stub can, for example, be mass produced on an automatic lathe from an elongate rod. The inventive blank thus includes a first part made from the material for the implant and a second part having the dimensional tolerances required for easy support.

The support stub can optionally be provided with certain structural features which enhance the process of fabricating the ultimate implant from the blank. In this respect, it must be kept in mind that the fabrication of inlays or crowns right in the dentist's office and in a single session involves the following considerations:

1. Each implant is a custom shaped piece unique to the particular patient.

2. There is no time for test runs; the implant has to fit properly after only one pass through the milling machine.

3. Different blanks required by the differing shape and/or function of different types of teeth have to be machined in a random order established by the needs of successive patients.

4. Insertion and handling is done manually, without any special tools.

In contrast, in an industrial environment, a machine is generally set up to make a large series of identical parts, and the process is always initialized by a test run. Once a first part comes out of the machine, it is carefully measured and then the machine and/or the tools are adjusted as required in order to attain the desired accuracy and finish. For a dentist, this trial and error procedure, which can last anywhere from 5 to 20 minutes, is highly undesirable.

Moreover, the shape of any tool will alter with wear, and something must be done to compensate for this effect. In industry, a gauge is periodically used on the machine to calibrate it and thus compensate for wear. According to the invention, the blank itself has structure which permits it to act as a gauge, so that calibration can be accomplished in an automatic fashion. In particular, according to the invention, calibration can be accomplished by touching the tool to a specific region of the blank which has known and accurate dimensions and can thus serve as a reference for the machine. The fact that touching has occurred is most easily noted by detecting a drop in the rotational speed of the tool, for example by using an optical or magnetic sensor.

Not just one but several such regions can be provided. By sequentially touching and sensing these regions on the blank, a code representing information about the shape and/or physical properties of the blank can be sensed. In the case of very hard alumina, often used for stress bearing structures, the machine can be told to precede the actual shaping by a scrub cycle. In the event no blank has been inserted, a situation expected to occasionally occur in the sometimes tense dental environment, the tool will touch nothing within a specified range and the machine can then alert the operator that a blank must be inserted. As an additional feature facilitating manual handling, the blank should be adapted to be secured in the machine chuck rapidly and without the need for extra tools such as a screwdriver or wrench.

Furthermore, it is desirable to design the blank in a way which allows its insertion only in a unique angular position. This feature makes it possible to use a blank which approximately resembles the end product, and to thus minimize wear on and run time of the machine.

DETAILED DESCRIPTION

Figure 1:
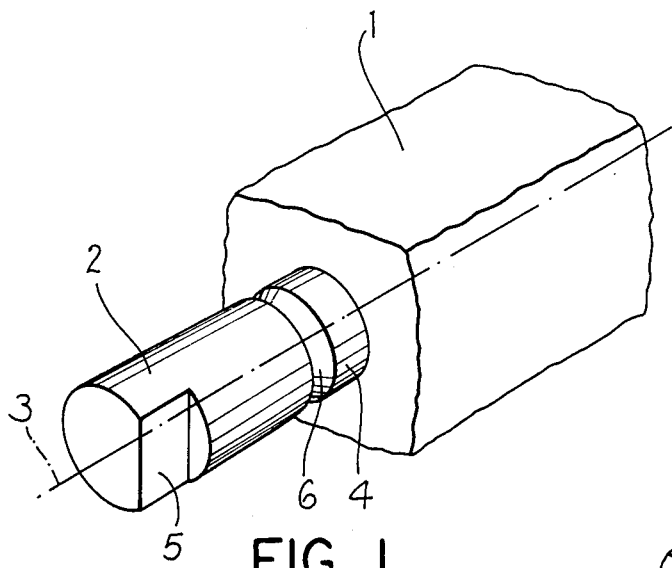
FIG. 1 is a perspective view of a blank which embodies the invention and which includes a piece of raw material and an attached stub.
Figure 4:
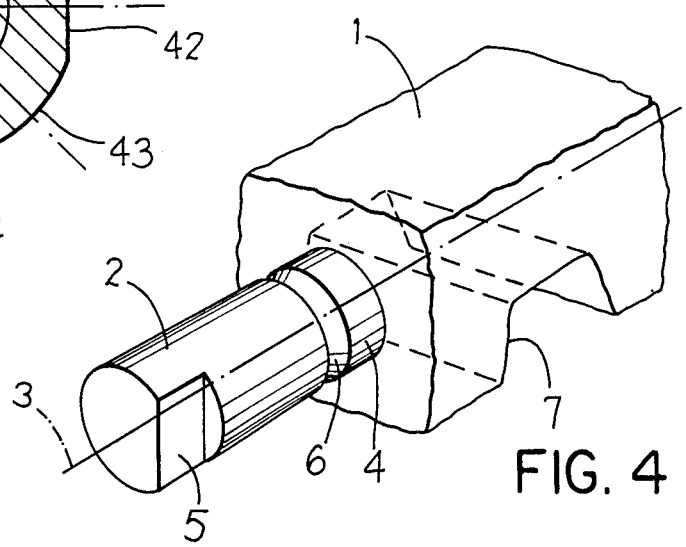
FIG. 4 is a perspective view of a further alternative embodiment of the blank of FIG. 1.

FIG. 1 shows a first version of the inventive blank. A part of machinable raw material 1, preferably ceramic silica, has been obtained by a baking process. This process yields a coarse contour which cannot easily be held by a simple gripping mechanism. A support stub 2 has therefore been cemented to the raw part 1 and establishes a common axis 3. The stub 2 has a reference section 4 which is a substantially cylindrical surface machined with great accuracy. This surface 4 can be used as a reference to calibrate the milling machine. Since the blank typically does not possess rotational symmetry, a radially facing keying surface 5 has been provided on the stub to permit a defined angular orientation of the blank to be established with respect to the machine. A groove 6 can further facilitate the gripping of the stub. In order to minimize wear on and run time of the milling machine, the blank can optionally be shaped to more closely resemble the final implant. For example, for the common case of a two lobed inlay, the blank could be shaped as shown in FIG. 4, the blank of FIG. 4 being identical to that of FIG. 1 except for the provision of a groove 7 in one side thereof.

Figure 2:
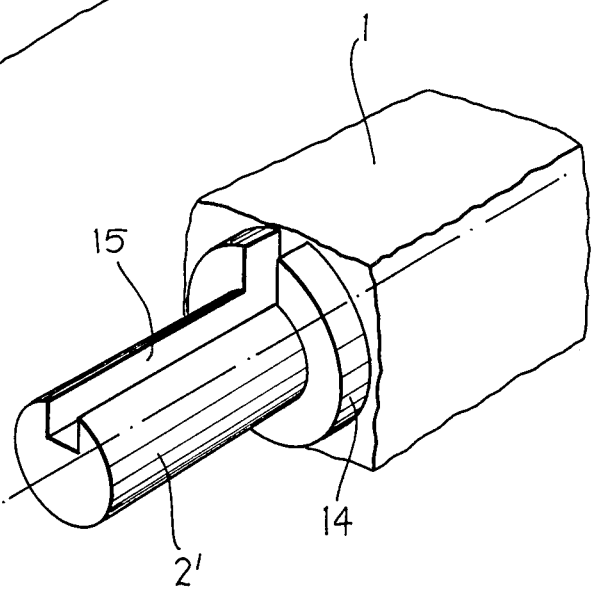
FIG. 2 is a perspective view similar to FIG. 1 of an alternative embodiment of the blank of FIG. 1 which is adapted for mass production.

Since it is desirable to tailor the blank for mass production, a refinement of the stub suitable for mass production is shown in FIG. 2. In FIG. 2, the coarse part 1 is identical to that of FIG. 1, but the stub 2 has, instead of the keying surface 5, a keying slot 15 which extends axially the full length of the stub 2'. This modification allows the stub 2' to be made from a preslotted rod using an automatic lathe. The functional features present in the embodiment of FIG. 1 have thus been maintained, while the fabrication has been simplified.

Figure 3:
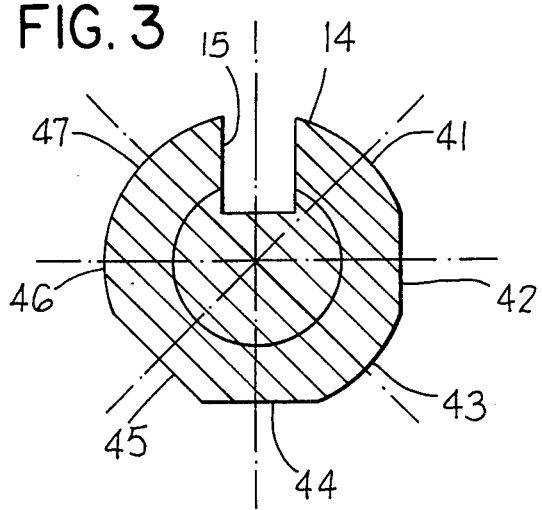
FIG. 3 is a sectional end view of a reference surface section of the blank of FIG. 2.

The size of the reference section, designated here by reference numeral 14, has been enlarged. This not only provides a larger bonding surface for securing the part 1 to the stub 2', but also permits additional features to be incorporated into the blank. FIG. 3 is a sectional view of the reference section 14 of the stub 2' of FIG. 2, which has an embedded code. The keying slot 5, which in FIG. 3 is located at twelve o'clock, ensures a predetermined angular orientation of the blank relative to the milling machine. Once the blank has been inserted, the machine will rotate the blank in steps of 45 degrees in a counterclockwise direction, which will initially bring the reference surface 41 to the twelve o'clock position. The machine will now slowly lower its milling tool, for example a grinding disc, while constantly monitoring the tool's rotational speed. As soon as there is contact between the tool and the stub, a distinct drop in tool speed will occur. (Contact could alternatively be sensed electrically). The speed drop indicates that the operating surface of the tool is now in contact with the reference surface 41 and, since the distance of the tool from the axis 3 is necessarily equal to the radius of the reference surface 41, the actual radius of the tool, which decreases with wear, can be determined. Note that this radial zeroing of the tool axis must be done with high accuracy, since any error is directly reflected in the final product. The angular orientation, of course, is defined precisely enough by the keying slot 15. The axial position of the tool relative to the blank is not critical.

Different blanks of various shapes and/or materials may be needed, some requiring a different machining routine. While it is conceivable that the operator could preset the machine each time for each specific blank, it is of greater convenience to let the blank carry the necessary information about itself. This can be accomplished in the following fashion. After the tool touches surface 41 it is retracted slightly and allowed to regain some or all of its free running speed. The blank is then rotated another 45 degrees so as to present reference surface portion 42. By advancing the tool and again sensing its speed, the machine can determine whether the radius of surface portion 42 is equal to or less than the radius of surface portion 41. For the sake of example, it is assumed that the machine can discriminate between these two different radiuses and thus read a binary code. For example, if the smaller radius represents a binary "1" and the larger radius a binary "0", then when the machine successively senses the radiuses of the surface portions 42 to 47 in FIG. 3 it will read a binary code of "101100". Different such binary codes can represent different characteristics of respective blanks.

The embodiments of the invention in which an exclusive property or privilege is claimed are defined as follows:

1. A blank from which an implant conforming to a cavity in a tooth can be machined by a milling machine, comprising a machinable part which is a block of a raw material for the implant and from which the entire implant is to be machined, and a supporting stub which is fixedly provided on and projects ourwardly from said machinable part, which can support said machinable part in the milling machine, and which can be discarded after the entire implant has been machined from said machinable part, wherein said supporting stub has thereon at a location spaced from said machinable part a cylindrical support surface concentric to an axis which extends through said supporting stub and through said machinable part, has keying means for facilitating a predetermined angular orientation of said supporting stub and said machinable part about said axis relative to the milling machine, and has thereon adjacent said machinable part an arcuate, radially outwardly facing reference surface which is concentric with said axis and which has a predetermined radius which conforms to precise dimensional tolerances at all location thereon.

2. The blank of claim 1, wherein said machinable part is made of a ceramic material, and wherein said supporting stub is made of metal and has an axially facing surface which is disposed against and adhesively secured to a surface of said machinable part.

3. The blank of claim 1, wherein said reference surface is substantially cylindrical and has a diameter substantially equal to the diameter of said cylindrical support surface, and wherein said supporting stub has therein a circumferential groove at a location axially between said cylindrical support surface and said cylindrical reference surface, and wherein said keying means includes a flat, radially outwardly facing surface provided at an end of said supporting stub remote from said machinable part.

4. The blank of claim 1, wherein said supporting stub has thereon coding surface means for physically representing information about characteristics of the material of said machinable part.

5. The blank of claim 4, wherein said supporting stub has at a location axially between said machinable part and said cylindrical support surface an approximately cylindrical reference section having a diameter greater than that of said cylindrical support surface, wherein said reference surface is provided at a first location on said reference section, and wherein said coding surface means includes a plurality of radially outwardly facing coding surface portions provided at respective second locations on said reference section which are spaced angularly from each other and from said first location, each said coding surface portion being spaced from said axis by one of two predetermined radial distances.

6. The blank of claim 5, wherein said keying means includes said supporting stub having a keying groove therein which extends axially therealong the full length thereof.

7. The blank of claim 1, wherein said machinable part has in one side thereof a groove which extends in a direction transverse to said axis.

8. A blank from which an implant for a cavity in a tooth can be machined by a milling machine, comprising: a machinable part made of a raw material for the implant and from which the entire implant is to be machined; and means for supporting said machinable part in the milling machine, including a supporting stub which is fixedly provided on said machinable part, which has been fabricated to precise dimensional tolerances to facilitate precise positioning of said machinable part in the milling maching during machining of the implant, and which can be discarded after the entire implant has been machined from said machinable part.

9. The blank of claim 8, wherein said supporting stub has a reference surface which is positioned thereon to precise tolerances and which a tool of the milling machine can engage to facilitate measurement of and compensation for tool wear.

10. The blank of claim 9, wherein said supporting stub includes surface means physically defining a code representing information about physical properties of said machinable part.

11. The blank of claim 8, wherein said machinable part is made of a ceramic material.

12. The blank of claim 8, wherein said machinable part and said supporting stub are separate parts and are joined to each other by an adhesive.

13. The blank of claim 8, wherein said supporting stub has a reference surface which is positioned thereon to precise tolerances and which can be engaged by a tool of the milling machine to facilitate a precise initial positioning of the tool relative to said blank.

14. The blank of claim 13, wherein said blank has an axis which extends through said supporting stub and said machinable part, wherein said supporting stub has keying means thereon for effecting a predetermined angular orientation of said blank in the milling machine with respect to said axis, wherein said supporting stub has a code surface portion shaped to define a code representing information relating to properties of said blank and capable of being read by the milling machine, and wherein said supporting stub has a generally cylindrical first section which is adjacent said machinable part, is concentric to said axis, and is of larger diameter than a cylindrical second section thereof which is concentric to said axis and spaced from said machinable part, said first section having an axially facing surface which is disposed against and secured to a surface of said machinable part and having thereon said reference surface and said code surface portion, and said second section having said keying means thereon.

15. The blank of claim 8, wherein said supporting stub has keying means thereon for facilitating a predetermined orientation of said blank in the milling machine.

16. The blank of claim 15, wherein said supporting stub has an axially symmetric outer periphery, and wherein said keying means includes keying surfaces formed in said outer periphery.

17. The blank of claim 8, wherein said supporting stub has a code surface portion shaped to define a code representing properties of said blank and capable of being read by the milling machine.

18. The blank of claim 8, wherein said supporting stub is made of metal.

19. A method of making a blank from which an implant for a cavity in a tooth can be machined by a milling machine, comprising the steps of: fabricating a machinable part which is made of a raw material and from which the entire implant is to be machined; fabricating a supporting stub which is adapted to support said machinable part in the milling machine, which conforms to precise dimensional tolerances in order to facilitate precise positioning of the machinable part in the milling machine during machining of the implant, and which can be discarded after the entire implant has been machined from said machinable part; and thereafter adhesively securing said supporting stub to said machinable part.

20. The blank of claim 19, wherein said step of fabricating said machinable part includes the steps of: compressively shaping a quantity of a ceramic material, and thereafter baking said quantity of ceramic material.

21. The blank of claim 19, wherein said step of fabricating said supporting stub includes the step of using an automatic lathe to machine said supporting stub.

* * * * *